United States Patent [19]

Surany

[11] Patent Number: 5,415,858
[45] Date of Patent: May 16, 1995

[54] PROCESS FOR CONTROLLING INSECT PESTS USING A STRAIN OF PROVINDENCIA

[76] Inventor: Paul Surany, 423 Green St., Durham, N.C. 22701-1607

[21] Appl. No.: 305,580

[22] Filed: Sep. 14, 1994

[51] Int. Cl.⁶ .................. A01N 63/00; C12N 1/12; C12N 1/20
[52] U.S. Cl. .................. 424/93.4; 435/252.1; 435/822; 424/93.1
[58] Field of Search .............. 435/252.1, 822; 424/93.1, 93.4

Primary Examiner—Marian C. Knode
Assistant Examiner—Kristin Larson
Attorney, Agent, or Firm—Olive & Olive

[57] ABSTRACT

A non-sporeforming enteric-type bacterium elaborates a regulatory substance that interacts with the insect's own neuro-secretory regulatory system at the time when the larvae of (holometamorphic) insects reach the prepupal stage. This bacterium is used to inhibit or interfere with the synthesis of chitin whereupon the affected insects are unable to complete their life cycle and die while at an immature stage.

10 Claims, No Drawings

PROCESS FOR CONTROLLING INSECT PESTS USING A STRAIN OF PROVINDENCIA

BACKGROUND OF THE INVENTION

1. Field of the Invention

This invention relates to microbial insecticides and in particular, to a non-sporeforming bacterial strain for use in insect control.

2. Description of the Related Art

Although numerous effective chemical insecticides have been developed in the attempt to decrease or eliminate undesired insects, there is a continued need for new insecticides. Chemical insecticides are often expensive, and may have toxic effects on humans and other animals other than insects. In addition, some 500 species of harmful insects, the vectors of transmissible diseases prominently included, have become resistant to most applicable synthetic insecticides.

Insects have been found to have natural infections caused by microorganisms such as *Bacillus pupillae* and *B. lentimorbus,* which appear to overwhelm the immature stages (grubs) of the Japanese beetle causing them to succumb to slow deaths. *Bacillus thuringiensis* produces a protein toxin in the form of a crystalline parasporal body, which causes paralysis of the gut, and finally death, of the larvae of many moths, butterflies, and other insects which have ingested the bacteria.

Bacterial insecticides, primarily utilizing *Bacillus thuringiensis,* have provided a means of controlling insect pests, such as insects of the order Lepidoptera, Coleoptera, and Diptera, in which the problem of resistance to man-made pesticides is one of the most acute. The *B. thuringiensis* cells are cultivated in large amounts to obtain a sufficient number of crystals, which are sprayed on crops to control the insects. Methods and compositions using *B. thuringiensis* which have been patented include, for example, the patent of Zaehner et al. (U.S. Pat. No. 5,277,906) for an insecticidal composition containing a carrier used against dipterous insects and a crystalline toxin from an asporous strain of *B. thuringiensis;* the patent of O'Brien et al. (U.S. Pat. No. 5,244,660) for a method of reducing the occurrence of certain darkling beetles; and other patents utilizing specific strains of *B. thuringiensis,* for example, U.S. Pat. Nos. 5,286,485; 5,262,160; 5,260,058; 5,211,946; 5,204,100 and 5,185,148.

Most other microorganisms are not known to have specific or substantial insecticidal activity, although it is of course possible that large, concentrated amounts of various substances produced by bacteria, or by any living organism, could be generally or specifically inhibitory to living things. The Enterobacteriaceae, particularly Proteus and Providencia and related microorganisms, while sometimes capable of producing various toxins, are not known to have specific insecticidal activity.

Various Proteus species and the closely related Providencia species are found in decaying matter, soil and water, while others are found in animal infections. Typically Proteus species spread rapidly in a nearly transparent, microscopic film of moisture on the surface of freshly poured agar or other media. This film is due to the actively motile swarming of typical peritrichous forms of Proteus. In contrast, Providencia species form small, discrete and more or less circular colonies.

Whether in context of insect microbiology or, more precisely, pathology, a survey of the technical literature fails to reveal a substantial etiologic relationship that has evolved between the insect hosts and the bacteria of the Proteus type. Applicant is only aware of one record relating to Proteus species, which refers to an ostensibly accidental relationship with the immature stages (caterpillars) of the gypsy moth.

It is therefore an object of this invention to provide an effective, microbial product for the control of insects utilizing a Proteus-like Providencia bacterial strain.

Other objects and advantages will be more fully apparent from the following disclosure and appended claims.

SUMMARY OF THE INVENTION

A non-sporeforming enteric-type bacterium, identified as Providencia sp., elaborates a regulatory principle, which is possibly a hormone analogue, that interacts with the insect's own neuro-secretory regulatory system at the time when the larvae of (holometamorphic) insects reach the prepupal stage. The net result, easily perceptible, is the inhibition of, or interference with, the synthesis of chitin whereupon the affected insects are unable to complete their life cycle and die while at an immature stage.

Other aspects and features of the invention will be more fully apparent from the following disclosure and appended claims.

DETAILED DESCRIPTION OF THE INVENTION AND PREFERRED EMBODIMENTS THEREOF

The present invention is a composition for control of insects and a method for controlling undesired insects.

The microorganism in question was isolated after the discovery of an epizootic disease among colonies of houseflies (*Musca domestica*) that had been kept since the early 1950's on the campus of the University of Illinois. The original ancestors of these insects had been trapped on Illinois farms and their progeny bred for the purpose of studying the genetics of resistance to (synthetic) pesticides, principally to chlorinated hydrocarbons, like DDT and its congeners. Examination of adult flies killed by the epizootic disease using standard microbiological assay methods yielded no explanation as to the cause of mortality. However, when the methodology was changed by keeping the plates (Petri dishes) under observation for ten to fourteen days (in contrast to the three-day limit usually observed in microbiology), a bacterium was isolated that, in subsequent tests, proved to be the causative agent capable of eliciting the epizootic.

The causative agent of the epizootic disease was shown to be a Providencia species (called herein "Providencia sp."), and was not previously described in accordance with the definitions listed in *Bergey's Manual of Determinative Bacteriology,* 6th Edition. The genus was positively identified on the Berkeley-campus of the University of California. Biochemical tests including urea hydrolysis, acid and sometimes gas production from mannitol, glucose, fructose, galactose, and adonitol, no fermentation of lactose and maltose, lack of liquefaction of gelation, alkalinity of growth in litmus milk, indole production, citrate utilization, and nitrite production from nitrates helped to place the species as being closely related to what was earlier classified as *Proteus rettgeri.* No serological tests and no DNA-sequencing were performed.

In 1962, Ewing (Ewing, W. H., 1962, Int. Bull. Bact. Nomencl. Taxon. 12:98–103) had split off the Proteus-like species from non-spreading colonies and had grouped them as members of the newly established genus of Providencia. Thenceforth, *Proteus rettgeri* has been properly identified as *Providencia rettgeri* (cf. *Bergey's Manual of Systematic Bacteriology*, v. 1, pp 492–496, 1984). The bacterial strain utilized in the invention is similar to the type strain of *Providencia rettgeri* in being a peritrichous, motile, Gram-negative rod and having essentially the same biochemical test results. Insect-controlling activity, however, according to the invention herein has not previously been found with other strains or isolates of this species.

This culture of Providencia sp., previously designated IL -55-2101, has been deposited at the American Type Culture Collection (12301 Parklawn Drive, Rockville, Md.) on Sep. 9, 1994 as ATCC No. 55610, prior to the filing date hereof, to be available to the public upon issuance of this application as a patent in accord with the Budapest Treaty on the International Recognition of the Deposit of Microorganisms for the Purposes of Patent Procedure.

The colonies of the concerned Providencia species are small, about 1–3 mm in diameter and they are easily missed amongst the mixed bacterial populations houseflies are known to harbor using standard microbiological assays. The color of the surface-growths on agar media, for example, on Nutrient Agar (BBL or Difco), is grayish and slightly translucent; the colonies turn opaque-white upon aging. Remarkably, aged cells remain recognizable for weeks and do not lyse.

Providencia sp. grows rather slowly on the surface of agar nutrient media and in order to obtain optimal growth on agar plates, the plates should be wrapped in plastic to avoid moisture loss for the 10–14 days required. However, in liquid, media containing common nutrients, e.g., Nutrient Broth (BBL) the cells proliferate luxuriantly. Thus, this bacterium can be produced in any desired quantities. For the preservation of the species a lyophilized culture is preferably kept in a frozen state.

The preferred method of use or of assay of unknown related microbial strains for the microbial control of insects is to add a liquid culture of Providencia sp. to the environment or medium in which the immature stages of the insect (e.g., Diptera) are developing. Within one week insect pathogenic or controlling activity is observed. Generally, use of a 48-hour broth culture is preferred. Alternatively, liquid growth media from which the cells of Providencia sp. have been removed after growth may be used.

Aside from the case when Providencia sp. has infected the target insects it seems to be capable of persisting in the environments as a saprophyte. It also appears that adult flies serve here as agents of dissemination, as passive carriers in the wild.

The active principle elaborated by Providencia sp. is secreted into the environment not unlike the bacterial exotoxin. Its mode-of-action is manifested by inhibiting, or interfering with, the formation of chitin that is an essential component of the exoskeleton of insects. Further examination of this Providencia sp. may reveal traits that parallel those of *Bacillus thuringiensis*. Thus, the ability to synthesize the toxic factor may be due to the presence in the cells of adventitious regulatory genetic codes to enable or compel the bacterial cells to synthesize the relevant toxic factor, and this synthetic ability may be horizontally transmissible to other cells which are more easily grown, such as *Pseudomonas fluorescens.* Providencia sp. differs, however, from *B. thuringiensis* in that there is no known crystalline precipitate in the former.

Aside from the prospect of separating out and then perhaps concentrating the active ingredient for application to the sites where harmful insects breed, liquid cultures of the bacterium may be applied to accumulations of organic wastes for the efficient control of flies. Such sites are landfills, discards of canning plants and/or farm areas where livestock is kept, because the control of flies is difficult with reliance on conventional methods.

An even more intriguing and rewarding potential use of Providencia sp. is to transfer of gene(s) from the bacterium, where they are responsible for the synthesis of the active ingredient, to cultivated plants with reliance on the already well-established DNA techniques, rendering the latter inherently, and heritably, agents of the control of injurious insects. With regard to pests having endophytic life habits such a measure would be critically important because they cannot be reached inside the plants with topically applied pesticides.

In general, the resort to agents of biological control of the pests and vectors of disease would decrease the burdening of the environment with biocides that have a broad-spectrum of effectiveness.

The features and advantages of the present invention will be more clearly understood by reference to the following examples, which are not to be construed as limiting the invention.

EXAMPLES

EXAMPLE I

A broth culture (about 5 ml) of Providencia sp. designated IL-55-2101 (ATCC 55610) is added to about ½ liter of the insect nutrient medium in which the larval stages (maggots) of the flies are growing and maturing. No unusual signs of pathogenicity are noticeable for the first four days. On the fifth day, when the larvae (maggots) are timed to pupate, drastic changes are noticeable in the prepupal stage. The last larval integument which is to participate in the formation of the pupa (pupa coarctate) in an untreated fly, remains only partly sclerotized in insect larvae treated with Providencia sp., thus exposing the central zone of the larval integument as practically unchanged. The whole prepupal habitus thus assumes a characteristic "dumb-bell" shape. Alternatively, some of the larval population treated with Providencia sp. is impaired before the pre-pupal stage and dies while exhibiting no contraction. All such affected immature stages die before the eight day.

EXAMPLE II

Providencia sp. (ATCC 55610) is tested on the larvae (grubs) of a dynastic beetle (*Oryctes rhinoceros*), a pest of coconut palms using about 20 ml of a 48-hour broth culture added to about 20 liters of a sawdust larval culture. The mortality rate of the beetles treated with Providencia sp. is 100%. All larvae died in the prepupal stage displaying symptoms what the French workers call as "recrocqueillement" (i.e. the shriveling of the body in a curved position).

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A process for controlling insect pests in the larval stage which comprises contacting said insect pests, or the location around said insect pests, with an insect-controlling amount of a medium in which cells of Providencia sp. ATCC No. 55610 have been grown.

2. The process according to claim 1 in which said cells have been removed from the medium.

3. The process according to claim 1 in which said medium contains cells of said Providencia sp. ATCC No. 55610.

4. The process according to claim 1, wherein said insect pests belong to the order Diptera.

5. The process according to claim 1, wherein said insect pests belong to the order Coleoptera.

6. A process for controlling insect pests in the larval stage comprising contacting said insect pests, or the location around said insect pests, with an insect-controlling effective amount of Providencia sp. ATCC No. 55610.

7. The process according to claim 6, wherein said insect pests belong to the order Diptera.

8. The process according to claim 6, wherein said insect pests belong to the order Coleoptera.

9. An insecticidal composition for use in the larval stage of insects comprising an insect-controlling amount of a medium in which cells of Providencia sp. ATCC No. 55610 have been grown.

10. A biological pure culture of Providencia sp. ATCC No. 55610.

* * * * *